United States Patent
Makovec et al.

[11] 4,004,008
[45] Jan. 18, 1977

[54] O-TERTIARY AMINO-ALKYL-N-BENZOYL TYROSIL AMIDES

[75] Inventors: Francesco Makovec, Taccona (Milan); Luigi Rovati, San Fruttuoso di Monza (Milan); Paolo Senin, Monza (Milan), all of Italy

[73] Assignee: Rotta Research Laboratorium S.p.A., San Fruttuoso di Monza (Milan), Italy

[22] Filed: Feb. 3, 1975

[21] Appl. No.: 546,481

[30] Foreign Application Priority Data

Feb. 1, 1974 Italy .................. 67286/74

[52] U.S. Cl. .................. 424/248.54; 424/250; 424/267; 424/274; 424/324; 424/247.2 A; 260/268 R; 260/268 H; 260/293.64; 260/293.71; 260/293.76; 260/326.25; 260/326.42; 260/326.43

[51] Int. Cl.² .................. C07D 295/12

[58] Field of Search .................. 260/247.2 A, 293.76, 260/293.64, 293.71, 268 R, 268 H, 326.75, 326.41, 247.2 B, 471 C, 559 A326.42, 326.43; 424/248, 250, 267, 274, 324

[56] References Cited

OTHER PUBLICATIONS

Bertaccini et al. Br. J. Pharmac. Vol. 34, p. 310 (1968).
S. Vanov Brit. J. Pharmacol. vol. 24, p. 591, 1965.
Berti et al. Arch. Int. Pharmacodyn. vol. 192, p. 247, (1971).
Janssen et al. J. Pharm. Pharmacol. vol. 9 p. 381 (1956).
Weikel et al. J. Pharmacol. & Exp. Therp. vol. 149, p. 161 (1965).
Jalon et al. Farmacoterapia Act. 3. p. 313 (1945).
Bertaccini et al. Europ. J. Pharmacol. vol. 22, p. 320 (1973).

Primary Examiner—Donald G. Daus
Assistant Examiner—Jose Tovar
Attorney, Agent, or Firm—Sughrue, Rothwell, Mion, Zinn & Macpeak

[57] ABSTRACT

Tyrosine derivatives of the formula:

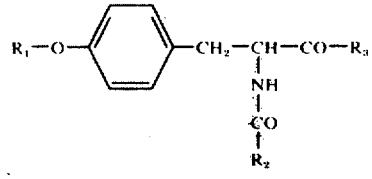

wherein: $R_1$ is a linear or branched-chain alkyl group having 1–6 carbon atoms, terminating by a tertiary amino group; $R_2$ is an unsubstituted, monosubstituted or di-substituted phenyl or benzyloxy group, the substituent being —Cl, —Br, —NO$_2$, —OCH$_3$, —CH$_3$ or —CF$_3$; $R_3$ is a primary, secondary or tertiary amino group or an aryl-alkylamino group having 7–9 carbon atoms; and salts of said tyrosine derivatives with pharmaceutically acceptable acids.

11 Claims, No Drawings

O-TERTIARY AMINO-ALKYL-N-BENZOYL TYROSIL AMIDES

This invention concerns tyrosine derivatives of the L; D,L; and D forms corresponding to the formula:

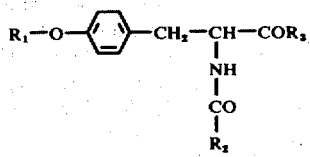

in which $R_1$ is an alkyl group selected from the class consisting of linear or branched-chain groups having 1 – 6 carbon atoms terminating by a tertiary amino group (e.g.: dimethylamino, diethylamino, di-n-propylamino, di-isopropylamino, di-isobutylamino, methylamino, pyrrolidino, piperidino, piperazino, N'substituted with alkylic, hydroxyalkilic, benzylic, etc. groups);
in which $R_2$ can be:
$A_2$: a simple phenyl group which may be mono- or bi-substituted in ortho-, meta-, or para-position with substituents chosen from the groups:

—Cl, —Br, —NO$_2$, —OCH$_3$, —CH$_3$, —CF$_3$;

$B_2$: a benzgloxy group, simple or mono- or bi-substituted in ortho—, meta—, or para— position with substituents selected from the groups: —Cl, —Br, —NO$_2$, —OCH$_3$, —CH$_3$, —CF$_3$; and in which $R_3$ may be:
$A_3$ : a primary amino group;
$B_3$ : a secondary amino group, especially a linear or branched chain aliphatic monoalkylamine with 1–6 carbon atoms (e.g.: methylamine, ethylamine, n-propylamine n-butylamine, n-hexylamine, isopropylamine, isobutylamine, etc.);
$C_3$ : a tertiary amino group, especially an aliphatic or alicylic dialkylamine containing 2 to 8 carbon atoms (e.g., dimethylamine, diethylamine, di-n-propylamine, di-n-butylamine, di-isobutylamine, methyl-ethylamine, pyrrolidine, piperidine, morpholine,);
$D_3$ : an aryl-alkylamine containing from 7 to 9 carbon atoms (e.g. benzylamine, phenylethylamine, etc.).

These tyrosine derivatives can preferably be salified with pharmaceutically acceptable acids thus rendering them hydrosoluble and therefore more stable for conservation. These acids may be:

a. inorganic acids, such for example as hydrochloric, phosphoric or sulphuric acid.

b. organic acids, such, for example, as citric, oxalic, acetic, maleic, fumaric, salicylic, nicotinic acid.

The compounds of this invention have been shown to possess in experimental animals a high antispastic pharmaceutical activity. In human beings this activity combines with an indirect analgesic activity, consequent upon solution of the spastic syndromes. Many of these components moreover show a vasodilactric action upon the peripheric and cerebral circle which is of particular significance for some of these.

The most favoured components are those in which:
a. $R_1$ is a linear alkylic group having 2 or 3 carbon atoms, and the tertiary amino group either diethylamine, pyrrolidine or N'-methyl-piperazine.
b. $R_2$ is a phenylic or benzyloxy group, which may be either simple or monosubstituted, in the para-position, with chlorine or methyl.
c. $R_3$ is a secondary amino group containing 3 or 4 carbon atoms, or else a tertiary amino group containing from 4 to 6 atoms.

The method of preparation of the tyrosine derivatives in which $R_2=A_2$; $R_3=A_3$, $B_3$, $C_3$, $D_3$ in the formula —DL— and of the tyrosine derivatives in which $R_2=B_2$; $R_3=A_3$, $B_3$, $C_3$, $D_3$ in the formulae L; DL; D consists of a series of conversions illustrated in diagram 1.

Diagram 1

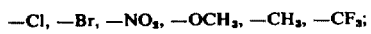

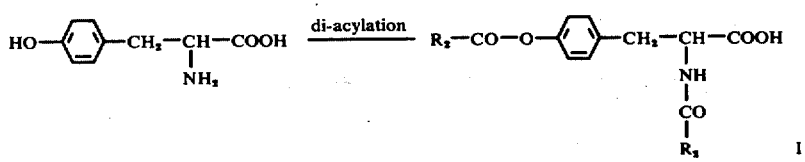

TYROSINE

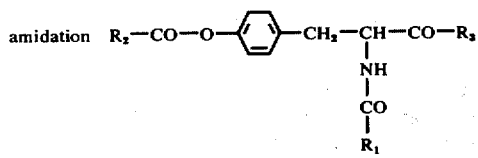

hydrolysis

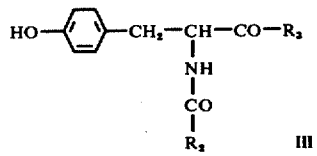
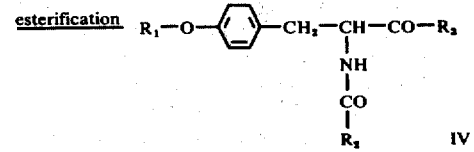

That is to say, the tyrosine is caused to react with only two moles of the suitable acylic chloride under Schotten-Baumann conditions, at a temperature between 0° and 10° for a period of between 2 and 12 hours to give the compounds of formula 1, i.e., the N-O- (di-acyl derivatives) of the tyrosine.

These compounds are then amidated by the mixed anhydride method, mixed in an inert solvent, as, for example, acetone, chloroform, dioxane, tetrahydrofurane, ethyl acetate, etc., at a temperature between −15° +15°, for a time varying between 2 and 24 hours, to give the corresponding formula II amides.

These amido-ether tyrosine derivatives of formula II are selectively hydrolized in an aqueous or hydroalcoholic medium in the presence of bases such as hydroxides, carbonates or bicarbonates of alkaline metals, at a temperature between 20° and 60°, during a period varying between 2 and 24 hours to give the diamidic tyrosine derivatives in formula III.

Finally, the compounds of formula IV are prepared by reaction between the tyrosine diamides of formula III and the haloalkylamine in the presence of sodium metal, sodium methylate or sodium amide in organic solvents such as acetone, benzol, toluene, dimethylsulphoxide, dimethylformamide ethylene glycol dimethyl ether, under reflux and in a period varying between 2 and 48 hours.

The method of preparing the tyrosine deivatives in which $R_2=A_2$; $R_3=A_3$, $B_3$, $C_3$, $D_3$ in the -L-and-D- forms consist of a series of sequences shown in the diagram 2:

nide, ethylene glycol dimethyl ether, under reflux and in a time varying between 2 and 48 hours.

EXAMPLE 1

O,N-(di-benzoyl)-L-tyrosine

To a solution of 18.1 g (0.1 moles) of L-tyrosine in 100 cc of NaCH 1 N brought to 5° C there are added in about 30 minutes, simultaneously, while agitating and keeping the reaction temperature between 5° C and 10° C, 200 cc of NaOH 1 N and 28.1 g (0.2 moles) of benzoyl chloride. This is left being agitated for 12 hours. It is acidified with HCl 2 N and filtered. It is recrystallized with 95% ethanol.

35 g. produced. Yield 88%. Melting point 208°–211°. $(\alpha)$ D 20 = 29 ± 2° (in tetrahydrofurane).

EXAMPLE 2

O,N-(di-benzoyl)-DL-tyrosil-di-n-propylamide 38.8 g (0.1 moles) of O,N-(di-benzoyl-L-tyrosine are dissolved in 300 ml of anhydro acetone; the solution is cooled to −10° C and added to it, under agitation, are 10.1 g (0.1 moles) of triethylamine; then there are added, still at −10° C, 10.8 g (0.2 moles) of ethyl chlorocarbonate. Temperature is kept at −10° C for 20 minutes, and then 10.1 g (0.1 moles) of di-n-propylamine are added. This is left under agitation for 6 hours, Diagram 2

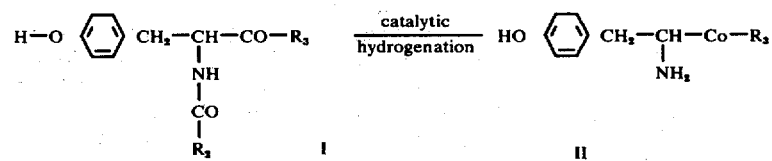

in which $R_3=B_3$ (prepared according to diagram 1).

Acylation

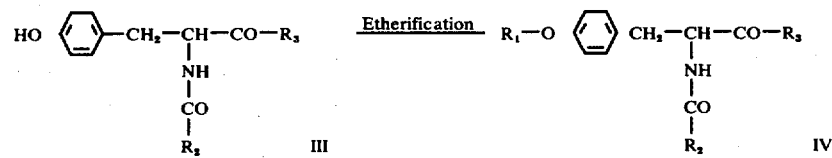

in which $R_2=A_2$                                in which $R_2=A_2$

That is, the N-carbobenzyloxy-amides of tyrosine (I) (for the preparation of these see diagram 1 compounds of type III) in which $R_2=B_2$ are decarbobenzyloxylated by catalytic hydrogenation at room temperature and atmospheric pressure, using as a catalyst palladium at 10% on carbon or palladium chloride to give the corresponding tyrosine amides (II). These amides (II) are acylated with a mole of a suitable acylic chloride under Schotten-Baumann conditions, at a temperature between 0° and 20° for between 2 and 12 hours to give the corresponding N-acyl-tyrosine amides in formula III (and in which $R_2=A_2$).

Finally, the compounds of formula IV (in which $R_2=A_2$) are prepared by reacting the N-acyl tyrosine amides (III) with the appropriate haloalkylamines in the presence of sodium metal, sodium methylate or sodium amide in organic solvents such as acetone, benzol, toluene, di-methyl-sulphoxide, dimethylformaincreasing the temperature to rise the room temperature; it is dried off and the residue is taken up with ethyl acetate.

It is washed with HCl 2 N, sodium bicarbonate and finally with water; then anhydrified on anhydro $Na_2SO_4$. By concentration at low volume and the addition of petroleum ether the product is precipitated.

Amount obtained 38.2 g. Yield 81%. Melting point 114°–116° (crystallises with Ethanol to 95%).

EXAMPLE 3

N-Benzoyl-DL-tyrosil-di-n-propylamide

To a solution of 47.2 g (0.1 moles) of O,N-di-benzoyl-di-n-propylamide in 300 cc of methanol is added, under agitation, 100 cc of NaOH 1 N; this is left in reaction under agitation for 6 hours; the solution is diluted with 500 cc of $H_2O$ and is acidified with HCl 2 N.

The recipitated solid is filtered and recrystallised by ethanol at 95%.

Amount obtained 34.2g. Yield 93%. Melting point 193° – 195°.

EXAMPLE 4 (CR 605)

O-(2-diethylamino-ethyl)-N-benzoyl-DL-tyrosil-di-n-propylamide 36.8g (0.1 moles) of N-benzoyl-DL-tyrosil-di-n-propylamide are suspended in 350 cc of toluene; there are then added, under agitation, 5.4g (0.1 moles) of sodium methylate and 50 cc (0.1 moles) of a titrated toluenic solution of 2-diethylamino-ethyl-chloride. The temperature is taken up to 105° C and the solution is left at this temperature, in agitation, for 12 hours. The toluenic solution is extracted with HCl 2N; the aqueous acid phase is alkalised, cold, with sodium carbonate, and then re-extracted with successive portions of ethyl acetate.

The reunited organic phases are anhydrified upon anhydrous $Na_2SO_4$, filtered and dried off. The oily residue which is obtained crumbles after a few hours of rest. Amount obtained 39.2g. Yield 84%. Melting point 65°–67°. (Crystallises with petroleum ether).

The free base can be salified so as to render it hydrosoluble. For this purpose for example it is dissolved in acetone and precipitated as an oxalate by the addition of a solution of oxalic acid in ethanol. Recrystallises with ethanol. Melting point (oxalate): 159°–162°. Alternatively it can be dissolved in acetone and precipitated with an acetone solution of HCl. Recrystallises with acetone-ethanol. Melting point (chlorhydrated): 181°–183°.

EXAMPLE 5 (CR 592)

O-(2dimethylamino-ethyl)-N-benzol-DL-Tyrosil-di-n-propilamide

Procedure as in Example 4, using 2-dimethylamino-ethyl-chloride instead of 2-diethylamino-ethyl-chloride. Finally the oily base is converted into oxalate.

Yield 84%. Melting point (oxalated): 169°–171° (crystallised by ethanol).

EXAMPLE 6 (CR 624)

O-(2-di-isopropylamino-ethyl)-N-benzoyl-DL-tyrosil-di-n-propylamide

Procedure as in Example 4, using 2-di-isopropylamino-ethyl-chloride instead of 2-diethylamino-ethyl-chloride. Finally the oily base is converted into oxalate.

Yield 78%. Melting point (oxalate): 154°–155° (crystallised by acetone).

EXAMPLE 7 (CR 823)

O-(2-di-n-propylamino-ethyl)-N-benzoyl-DL-tyrosil-di-n-propylamide

Procedure as in Example 4, using 2-di-n-propylamino-ethyl-chloride in place of 2-diethylamino-ethyl-chloride. Finally the oily base is converted into oxalate.

Yield 79%. Melting point (oxalate): 128°–130° (crystallised by acetone).

EXAMPLE 8 (CR 816)

O-(3-dimethylamino-propyl)-N-benzoyl-DL-tyrosil-di-n-propylamide

Procedure as in Example 4, using 3-dimethylamino-propyl-chloride instead of 2-diethylamino-ethylchloride.

Finally the oily base is converted into oxalate.

Yield 81%. Melting point (oxalate): 112°–114° (crystallised by acetone).

EXAMPLE 9 (CR 829)

O-(4-diethylamino-butyl)-N-benzoyl-DL-tyrosil-di-n-propylamide

Procedure as in Example 4, using 4-diethylamino-butyl-chloride instead of 2-diethylamino-ethyl chloride.

Finally the oily base is converted into oxalate.

Yield 76%. Melting point (oxalate): 107°–110° (crystallised by acetone-ether).

EXAMPLE 10 (CR 607)

O-(3-dimethylamino-propyl)-N-benzoyl-DL-tyrosil-di-n-propylamide

Procedure as in Example 4, using 3-dimethylamino-propyl chloride instead of 2-dimethylamino-ethyl-chloride.

Finally the oily base is directly converted into oxalate.

Yield 83%. Melting point (oxalate): 120°–123° (crystallised by acetone).

EXAMPLE 11 (CR 625)

O-(2-pyrrolidil-N'-ethyl)-N-benzoyl-DL-tyrosil-di-n-propylamide

Procedure as in Example 4, using N- (2-chloroethyl)-pyrrolidine instead of 2-diethylamino-ethyl-chloride.

Finally the oily base is directly converted into oxalate.

Yield 80%. Melting point (oxalate): 185°–187° (crystallised by ethanol-acetone).

EXAMPLE 12 (CR 630) O-(2-piperidil-N'-ethyl)-N-benzoyl-DL-tyrosil-di-n-propylamide Procedure as in Example 4, using N-(2-chloroethyl)-piperidine instead of 2-diethylamino-ethy-chloride.

Finally the oily base is directly converted into oxalate.

Yield 79%. Melting point (oxalate): 175°–177°.

EXAMPLE 13 (CR 609) O-[3-(N''-hydroxy ethyl-piperazine)-N'-propyl]-N-benzoyl-DL-tyrosil-di-n-propylamide Procedure as in Example 4, using N-3-chloropropyl-N'-2-hydroxy-ethyl-piperazine instead of 2-diethylamino-ethyl-chloride.

Finally the oily base is directly converted into oxalate.

Yield 73%. Melting point-(oxalate): 193°–195° C (Crystallised by ethanol).

EXAMPLE 14 (CR 619) O-[3-(N''-benzyl piperazine)-N'-propyl]-N-benzoyl-DL-tyrosil-di-n-propylamide Procedure as in Example 4, using N-3-chloropropyl-N'-benzyl-piperazine instead of 2-diethylamino-ethyl-chloride.

Finally the oily base is directly converted into oxalate.

Yield 75%. Melting point (oxalate): 242°–245°.

EXAMPLE 15 (CR700) O-(3-diethylamino-1,2-dimethyl-propyl)-N-benzoyl-DL-tyrosil-di-n-propylamide Procedure as in Example 4, using 3-diethylamino-1,2-dimethyl-propyl-chloride instead of 2-diethylamino-ethyl-chloride.

Finally the oily base is directly converted into oxalate.

Yield 69%. Melting point (oxalate): 103°–106°.

EXAMPLE 16

O,N-(di-benzoyl)-DL-tyrosil-amide

Procedure as in Example 2, using aqueous ammonia instead of di-n-propylamine.

Yield 70%. Melting point 246°–248°.

EXAMPLE 17

N-benzoyl-DL-tyrosil-amide

Procedure as in Example 3.
Yield 94%. Melting point 234°–236°.

EXAMPLE 18 (CR740)

O-(2-dietylamino-ethyl)-N-benzoyl-DL-tyrosil-amide

Procedure as in Example 4, using N-benzoyl-DL-tyrosilamide instead of N-benzoyl-DL-tyrosil-di-n-propylamide.

Finally obtaining the solid base by recrystallising with acetone.

Yield 77%. Melting point (base): 155°–158°.

EXAMPLE 19

O,N-(di-benzoyl)-DL-tyrosil-di-n-methylamide

Procedure as in Example 2, using di-methylamine instead of di-n-propylamine.

Yield 78%. Melting point 212°–215°.

EXAMPLE 20

N-benzoyl-DL-tyrosil-di-methylamide

Procedure as in Example 3.
Yield 94%. Melting point 237°–239° (crystallised by methanol).

EXAMPLE 21 (CR 738)

O-(2-diethylamino-ethyl)-N-benzoyl-DL-tyrosil-di-methylamide

Procedure as in Example 4 using N-benzoyl-DL-tyrosil-dimethylamide instead of N-benzoyl-DL-tyrosil-di-n-propylamide.

Finally the oily base is directly converted into oxalate.

Yield 80%. Melting point (oxalate): 86°–88°.

EXAMPLE 22

O,N-(di-benzoyl)-DL-tyrosil-ethylamide

Procedure as in Example 2 using ethylamine instead of di-n-propylamine.

Yield 76%. Melting point 240°–243°.

EXAMPLE 23

N-benzoyl-DL-tyrosil-ethylamide

Procedure as in Example 3.
Yield 91%. Melting point 200°–203°, (crystallised by methanol).

EXAMPLE 24 (CR 608)

O-(2-dimethylamino-ethyl)-N-benzoyl-DL-tyrosil-ethylamide

Procedure as in Example 4 using N-benzoyl-DL-tyrosilethylamide instead of N-benzoyl-DL-tyrosil-di-n-propylamide and 2-dimethylamino-ethyl-chloride instead of 2-dietylaminoethyl-chloride.

Finally the oily base is directly converted into oxalate.

Yield 81%. Melting point (oxalate): 148°–149°.

EXAMPLE 25 (CR 711)

O-(2-diisopropylamino-ethyl)-N-benzoyl-DL-tyrosil-ethylamide

Procedure as in Example 4, using N-benzoyl-DL-tyrosil-ethylamide instead of N-benzoyl-DL-tyrosil-di-n-propylamide and using 2-di-isopropylamino-ethyl-chloride instead of 2-diethylamino-ethylchloride.

Finally the solid base is obtained by recrystallisation with acetone.

Yield 76%. Melting point (base): 173°–175°.

EXAMPLE 26

O,N-(di-benzoyl)-DL-tyrosil-n-propylamide

Procedure as in Example 2, using n-propylamine instead of di-n-propylamine.

Yield 78%. Melting point 221°–224°.

EXAMPLE 27

N-benzoyl-DL-tyrosil-n-propylamide

Procedure as in Example 3.
Yield 92%. Melting point 169°–171°. (Crystallised by ethanol).

EXAMPLE 28 (CR 821)

O-(2-pyrrolidil-N'-ethyl)-N-benzoyl-DL-tyrosil-n-propylamide

Procedure as in Example 4, using N-benzoyl-DL-tyrosil-n-propylamide instead of N-benzoyl-DL-tyrosil-di-n-propylamide and using N-(2-chloroethyl)-pyrrolidine instead of 2-diethylaminoethylchloride.

Finally the solid base is obtained by recrystallisation with acetone.

Yield 76%. Melting point (base): 169°–172°.

EXAMPLE 29

O,N-(di-benzoyl)-DL-tyrosil-di-ethylamide

Procedure as in Example 2, using di-ethylamine instead of di-n-propylamine.

Yield 82%. Melting point 154°–157°.

EXAMPLE 30

N-benzoyl-DL-tyrosil-di-ethylamide

Procedure as in Example 3.
Yield 93%. Melting point 196°–198°. (Crystallised by ethanol — H₂O).

EXAMPLE 31 (CR 734)

O-(2-diethylamino-ethyl)-N-benzoyl-DL-tyrosil-di-ethylamide

Procedure as in Example 4, using N-benzoyl-DL-tyrosil-di-ethylamide instead of N-benzoyl-DL-tyrosil-di-n-propylamide.

Finally the oily base is directly converted into oxalate.

Yield 82%. Melting point (oxalate): 115°–117°.

EXAMPLE 32 (CR 736)

O-[2-(N″-methyl-piperazine)-N′-ethyl]-N-benzoyl-DL-tyrosildiethylamide

Procedure as in Example 4, using N-benzoyl-DL-tyrosil-di-ethylamide instead of N-benzoyl-DL-tyrosil-di-n-propylamide and using N-2-chloroethyl-N′-methyl-piperazine instead of 2-diethylamino-ethylchloride.

Finally the solid base is obtained by recrystallisation with acetone.

Yield 75%. Melting point (base): 98°–100°.

EXAMPLE 33

O,N-(di-benzoyl)-DL-tyrosil-n-butylamide

Procedure as in Example 2, using n-butylamine instead of di-n-propylamine.

Yield 80%. Melting point 189°–192°. (Crystallised by ethanol).

EXAMPLE 34

N-benzoyl-DL-tyrosil-n-butylamide

Procedure as in Example 3
Yield 92%. Melting point 158°–160°. (Crystallised by ethanol 80%).

EXAMPLE 35 (CR 648)

O-(2-pyrrolidil-N′-ethyl)-N-benzoyl-DL-tyrosil-n-butylamide

Procedure as in Example 4, using N-benzoyl-DL-tyrosil-n-butylamide instead of N-benzoyl-DL-tyrosil-di-n-propylamide and using N-(2-chloroethyl)-pyrrolidine instead of 2-diethylamino-ethylchloride.

Finally the oily base is directly converted into oxalate.

Yield 79%. Melting point (oxalate): 182°–184°.

EXAMPLE 36 (CR 702)

O-[3-(N″-methyl-piperazine)-N′-propyl]-N-benzoyl-DL-tyrosil-n-butylamide

Procedure as in Example 4, using N-benzoyl-DL-tyrosil-n-butylamide instead of N-benzoyl-DL-tyrosil-di-n-propylamide and using N-3-chloropropyl-N′-methyl-piperazine instead of 2-diethylamine-ethylchloride.

Finally the oily base is directly converted into oxalate.

Yield 82%. Melting point (oxalate): 223°–225°.

EXAMPLE 37 (CR 786)

O-(2-diethylamine-ethyl)-N-benzoyl-DL-tyrosil-n-butylamide

Procedure as in Example 4, using N-benzoyl-DL-tyrosil-n-butylamide instead of N-benzoyl-DL-tyrosil-di-n-propylamide.

Finally the solid base is obtained by recrystallisation with acetone-ligroin.

Yield 81%. Melting point (base): 123°–125°.

EXAMPLE 38

O,N-(di-benzoyl)-DL-tyrosil-n-hexylamide

Procedure as in Example 2, using n-hexylamine instead of di-n-propylamine.

Yield 74%. Melting point 163°–165°. (Crystallised by ethanol).

EXAMPLE 39

N-benzoyl-DL-tyrosil-n-hexylamide

Procedure as in Example 3.
Yield 89%. Melting point 153°–155°. (Crystallised by ethanol).

EXAMPLE 40 (CR 825)

O-(2-pyrrolidil-N′-ethyl)-N-benzoyl-DL-tyrosil-n-hexylamide

Procedure as in Example 4, using N-benzoyl-DL-tyrosil-n-hexylamide instead of N-benzoyl-DL-tyrosil-di-n-propylamide and using N-2-chloro-ethyl-pyrrolidine instead of 2-diethylaminoethylchloride.

Finally the solid base is obtained by recrystallisation with acetone.

Yield 74%. Melting point (base): 135°–137°.

EXAMPLE 41

O,N-(di-benzoyl)-DL-tyrosil-benzylamide

Procedure as in Example 2, using benzylamine instead of di-n-propylamine.

Yield 77%. Melting point 262°–265°(Crystallised by methanol).

EXAMPLE 42

N-benzoyl-DL-tyrosil-benzylamide

Procedure as in Example 3.
Yield 90%. Melting point 238°–240° C. (Crystallised by methanol).

EXAMPLE 43 (CR 616)

O-(2-dimethylamino-ethyl)-N-benzoyl-DL-tyrosil-benzylamide

Procedure as in Example 4, using N-benzoyl-DL-tyrosilbenzylamide instead of N-benzoyl-DL-tyrosil-di-n-propylamide and using 2-dimethylamino-ethylchloride instead of 2-diethylamine-ethylchloride.

Finally the oily base is directly converted into chlorohydrate.

Yield 82%. Melting point (chlorohydrate): 189°–190°.

EXAMPLE 44

O,N-di-benzoyl-DL-tyrosil-pyrrolidilamide

Procedure as in Example 2, using pyrrolidine instead of di-n-propylamine.

Yield 74%. Melting point 160°–163°. (Crystallised by ethanol).

EXAMPLE 45

N-benzoyl-DL-tyrosil-pyrrolidilamide

Procedure as in Example 3.
Yield 88%. Melting point 200°–202°.

EXAMPLE 46 (CR 614)

O-(2-diethylamino-ethyl)-N-benzoyl-DL-tyrosil-pyrrolidilamide

Procedure as in Example 4, using N-benzoyl-DL-tyrosil-pyrrolidilamide instead of N-benzoyl-DL-tyrosil-di-n-propylamide.
Finally the oily base is directly converted into oxalate.
Yield 79%. Melting point (oxalate): 170°–174°.

EXAMPLE 47

O,N-(di-benzoyl)-DL-tyrosil-morpholilamide

Procedure as in Example 3.
Yield 89%. Melting point 229°–231°. (Crystallised by methanol).

EXAMPLE 48

N-benzoyl-DL-tyrosil-morpholilamide

Procedure as in Example 3.
Yield 89%. Melting point 229°–231°. (Crystallised by methanol).

EXAMPLE 49 (CR 611)

O-(2-dimetylamino-ethyl)-N-benzoyl-DL-tyrosil-morpholilamide

Procedure as in Example 4, using N-benzoyl-DL-tyrosil-morpholilamide instead of N-benzoyl-DL-tyrosil-di-n-propylamide and using 2-dimethylamino-ethylchloride instead of 2-diethylamino-ethylchloride.
Finally the oily base is directly converted into chlorohydrate.
Yield 80%. Melting point (chlorohydrate): 196°–197°.

EXAMPLE 50

O,N-(di-toluoyl)-L-tyrosine

Procedure as in Example 1, using toluoyl chloride instead of benzoyl chloride.
Yield 89%. Melting point 176°–178°. (Crystallised by ethanol). $(\alpha)_D^{20} = +23\pm2$ (in tetrahydrofurane.)

EXAMPLE 51

O,N-(di-toluoyl)-DL-tyrosil-di-n-propylamide

Procedure as in Example 2, using O,N-(di-toluoyl)-L-tyrosine instead of O,N(di-benzoyl)-L-tyrosine.
Yield 80%. Melting point 169°–173°. (Crystallised by ethanol).

EXAMPLE 52

N-toluoyl-DL-tyrosil-di-n-propylamide

Procedure as in Example 3.
Yield 91%. Melting point 193°–196°. (Crystallised by ethanol).

EXAMPLE 53 (CR 615)

O-(2-dimethylamino-ethyl)-N-toluoyl-DL-tyrosil-di-n-propylamide

Procedure as in Example 4, using N-toluoyl-DL-tyrosil-di-n-propylamide instead of N-benzoyl-DL-tyrosil-di-n-propylamide and using 2-dimethylamino-ethylchloride instead of 2-diethylamino-ethylchoride.
Finally the oily base is directly converted into oxalate.
Yield 82%. Melting point (oxalate): 185°–187°.

EXAMPLE 54 (CR 650)

O-(2-pyrrolidil-N'-ethyl)-N-toluoyl-DL-tyrosil-di-n-propylamide

Procedure as in Example 4, using N-toluoyl-DL-tyrosil-di-n-propylamide instead of N-benzoyl-DL-tyrosil-di-n-propylamide and using N-(2-chloroethyl)-pyrrolidine instead of 2-diethylamino-ethylchloride.
Finally the oily base is directly converted into oxalate.
Yield 77%. Melting point (oxalate): 159°–161°. (Crystallised by acetone-alcohol).

EXAMPLE 55 (CR 807)

O-(2-diethylamino-ethyl)-N-toluoyl-DL-tyrosil-di-n-propylamide

Procedure as in Example 4, using N-toluoyl-DL-tyrosil-di-n-propylamide instead of N-benzoyl-DL-tyrosil-di-n-propylamide.
Finally the oily base is directly converted into oxalate.
Yield 83%. Melting point (oxalate): 146°–149°.

EXAMPLE 56

O,N-(di-toluoyl)-DL-tyrosil-N-butylamide

Procedure as in Example 2, using O,N-(di-toluoyl)-L-tyrosine instead of O,N-(di-benzoyl)-L-tyrosine.
Yield 85%. Melting point 190°–193°. (Crystallised by ethanol).

EXAMPLE 57

N-toluoyl-DL-tyrosil-n-butylamide

Procedure as in Example 3.
Yield 91%. Melting point 174°–176°. (Crystallised by ethanol).

EXAMPLE 58 (CR 651)

O-(2-pyrrolidil-N'-ethyl)-N-toluoyl-DL-tyrosil-n-butylamide

Procedure as in Example 4, using N-toluoyl-DL-tyrosil-n-butylamide instead of N-benzoyl-DL-tyrosil-di-n-propylamide and using N-(2-chloroethyl)-pyrrolidine instead of 2-diethylamino-ethylchloride.
Finally the oily base is directly converted into oxalate.
Yield 80%. Melting point (oxalate): 161°–163°.

EXAMPLE 59 (797)

O-(3-pyrrolidil-N'-propyl)-N-toluoyl-DL-tyrosil-n-butylamide

Procedure as in Example 4, using N-toluoyl-DL-tyrosil-n-butylamide instead of N-benzoyl-DL-tyrosil-di-n-propylamide and using N-(3-chloropropyl)-pyrrolidine instead of 2-diethylamino-ethylchloride.

Finally the oily base is directly converted into oxalate.

Yield 78%. Melting point (oxalate): 147°–150°.

EXAMPLE 60 (CR 709)

O-(2-diisopropylamino-ethyl)-N-toluoyl-DL-tyrosil-n-butylamide

Procedure as in Example 4, using N-toluoyl-DL-tyrosil-n-butylamide instead of N-benzoyl-DL-tyrosil-di-n-propylamide and using 2-di-isopropylamino-ethylchloride instead of 2-diethylamino-ethylchloride.

Finally the solid base is obtained by recrystallisation with acetone-isopropylether-isopropanol.

Yield 73%. Melting point (base): 145°–147°.

EXAMPLE 61

O,N-(di-toluoyl)-DL-tyrosil-n-hexylamide

Procedure as in Example 2, using O,N-(di-toluoyl)-L-tyrosine instead of O,N-(di-benzoyl)-L-tyrosine and using n-hexylamine instead of di-n-propylamine.

Yield 76%. Melting point 177°–180°. (Crystallised by methanol).

EXAMPLE 62

N-toluoyl-DL-tyrosil-n-hexylamide

Procedure as in Example 3.

Yield 90%. Melting point 162°–164°. (Crystallised by methanol).

EXAMPLE 63 (CR 826)

0-(2-pyrrolidil-N'-ethyl)-N-toluoyl-DL-tyrosil-n-hexylamide

Procedure as in Example 4, using N-toluoyl-DL-tyrosil-n-hexylamide instead of N-benzoyl-DL-tyrosil-di-n-propylamide and using N-(2-chloroethyl)-pyrrolidine instead of 2-diethylamino-ethylchloride.

Finally the solid base is obtained by recrystallisation with acetone.

Yield 74%. Melting point (base): 137°–139°.

EXAMPLE 64

O,N-di-(p-chloro-benzoyl)-L-tyrosine

Procedure as in Example 1, using p-chloro-benzoyl-chloride instead of benzoyl-chloride.

Yield 87%. Melting point 207°–209°. (Crystallised by ethanol). $(\alpha)_D^{20} = +6 \pm 2$ (in tetrahydrofurane)

EXAMPLE 65

O,N-(di-p-chloro-benzoyl)-DL-tyrosil-di-n-propylamide

Procedure as in Example 2, using O,N-(di-p-chlorobenzoyl)-L-tyrosine instead of O,N(di-benzoyl)-L-tyrosine.

Yield 81%. Melting point 148°–151°. (Crystallised by ethanol).

EXAMPLE 66

N-(p-chloro-benzoyl)-DL-tyrosil-di-n-propylamide

Procedure as in Example 3.

Yield 90%. Melting point 202°–204°. (Crystallised by methanol).

EXAMPLE 67 (CR 716)

O-(2-diethylamino-ethyl)-N-(p-chloro-benzoyl)-DL-tyrosil-di-n-propylamide

Procedure as in Example 4, using N-(p-chloro-benzoyl)-DL-tyrosil-di-n-propylamide instead of N-benzoyl-DL-tyrosil-di-n-propylamide.

Finally the oily base is directly converted into oxalate.

Yield 83%. Melting point (oxalate): 128°–130°. (Crystallised by acetone.

EXAMPLE 68 (CR 725)

O-[3-(N''-methyl-piperazine)-N'-propyl]-N-(p-chloro-benzoyl)-DL-tyrosil-di-n-propylamide Procedure as in Example 4, using N-(p-chloro-benzoyl)-DL-tyrosil-di-n-propylamide instead of N-benzoyl-DL-tyrosil-di-n-propylamide and using N-3-chloro-propyl-N'-methyl-piperazine instead of 2-diethylamino-ethyl-chloride.

Finally the oily base is directly converted into citrate.

Yield 84%. Melting point (citrate): 117°–119°. (Crystallised by acetone).

EXAMPLE 69 (CR 727)

O-(2'-di-isopropylamino-ethyl)-N-(p-chloro-benzoyl)-DL-tyrosil-di-n-propylamide

Procedure as in Example 4, using N-(p-chloro-benzoyl)-DL-tyrosil-di-n-propylamide instead of N-benzoyl-DL-tyrosil-di-n-propylamide and using 2-diisopropylamino-ethylchloride instead of 2-diethylamine-ethylchloride.

Finally the oily base is directly converted into oxalate.

Yield 75%. Melting point (oxalate): 154°–156°.

EXAMPLE 70 (CR 733)

O-[2'-(N''-methyl-piperazine)-N'-ethyl]-N-(p-chloro-benzoyl)-DL-tyrosil-di-n-propylamide Procedure as in Example 4, using N-(p-chloro-benzoyl)-DL-tyrosil-di-n-propylamide instead of N-benzoyl-DL-tyrosil-di-n-propylamide and using N-2-cloro-ethyl-N'-methyl-piperazine instead of 2-diethylamino-ethylchloride.

Finally the oily base is directly converted into citrate.

Yield 79%. Melting point (citrate): 99°–101°.

EXAMPLE 71

O,N-(di-p-chloro-benzoyl)-DL-tyrosil-ethylamide

Procedure as in Example 2, using O,N-(di-p-chloro-benzoyl)-L-tyrosine instead of O,N-(di-benzoyl)-L-tyrosine and using ethylamine instead of di-n-propylamine.

Yield 76%. Melting point 196°–200°.

EXAMPLE 72

N-(p-chloro-benzoyl)-DL-tyrosil-ethylamide

Procedure as in Example 3.

Yield 92%. Melting point 171°–173°. (Crystallised by ethanol).

EXAMPLE 73 (CR 714)

O-[3-(N''-methyl-piperazine)-N'-propyl]-N-(p-chloro-benzoyl)-DL-tyrosil-ethylamide Procedure as in Example 4, using N-(p-chloro-benzoyl)-DL-tyrosil-ethylamide instead of N-benzoyl-DL-tyrosil-di-n-propylamide and using N-3-chloropropyl-N'-methyl-piperazine instead of 2-diethylamino-ethylchloride.

Finally the solid base is obtained by recrystallisation with acetone.

Yield 70%. Melting point (base): 178°–180°.

EXAMPLE 74

O,N-(di-p-chloro-benzoyl)-DL-tyrosil-n-butylamide

Procedure as in Example 2, using O,N-di-(p-chloro-benzoyl)-L-tyrosine instead of O,N-(di-benzoyl)-L-tyrosine, and using n-butylamine instead of di-n-propylamine Yield 79%. Melting point 199°–202°.

EXAMPLE 75

N-(p-chloro-benzoyl)-DL-tyrosil-n-butylamide

Procedure as in Example 3.

Yield 90%. Melting point 190°–192°. (Crystallised by ethanol 95%).

EXAMPLE 76 (CR 705)

O-[3-(N''-methyl-piperazine)-N'-propyl]-N-(p-chloro-benzoyl)-DL-tyrosil-n-butylamide Procedure as in Example 4, using N-(p-chloro-benzoyl)-DL-tyrosil-n-butylamide instead of N-benzoyl-DL-tyrosil-di-n-propylamide and using N-3-chloropropyl-N'-methyl-piperazine instead of 2-diethylamino-ethyl chloride.

Finally the solid base is obtained by recrystallisation with acetone.

Yield 73%. Melting point (base): 149°–151°.

EXAMPLE 77 (CR 729)

O-(2-diethylamino-ethyl)-N-(p-chloro-benzoyl)-DL-tyrosil-n-butylamide

Procedure as in Example 4, using N-(p-chloro-benzoyle)-DL-tyrosil-n-butylamide instead of N-benzoyl-DL-tyrosil-di-n-propylamide.

Finally the solid base is obtained by recrystallisation with acetone.

Yield 76%. Melting point (base): 109°–112°.

EXAMPLE 78 (CR730)

O-[2-(N''-methyl-piperazine)-N'-ethyl]-N-(p-chloro-benzoyl)-DL-tyrosil-n-butylamide Procedure as in Example 4, using N-(p-chloro-benzoyl)-DL-tyrosil-n-butylamide instead of N-benzoyl-DL-tyrosil-di-n-propylamide and using N-2-chloroethyl-N'-methyl-piperazine instead of 2-diethylamino-ethylchloride Finally the solid base is obtained by recrystallisation with acetone.

Yield 74%. Melting point (base): 147°–149°.

EXAMPLE 79 (CR 812)

O-(2'-pyrrolidil-N'-ethyl)-N-(p-chloro-benzoyl)-DL-tyrosil-n-butylamide

Procedure as in Example 4, using N-(p-chloro-benzoyl)-DL-tyrosil-n-butylamide instead of N-benzoyl-DL-tyrosil-di-n-propylamide and using N-(2-chloroethyl)-pyrrolidine instead of 2-diethylamino-ethylchloride.

Finally the solid base is obtained by recrystallisation with ethyl acetate.

Yield 72%. Melting point (base): 162°–164°.

EXAMPLE 80

O,N-(di-o-chloro-benzoyl)-L-tyrosine

Procedure as in Example 1, using o-chloro-benzoyl chloride instead of benzoyl chloride.

Yield 81%. Melting point 177°–180°. (Crystallised by ethanol 99%). $(\alpha)_D^{20} = +9\pm2$ (in tetrahydrofurane).

EXAMPLE 81

O,N-(di-o-chloro-benzoyl)-DL-tyrosil-di-n-butylamide

Procedure as in Example 2, using O,N-(di-o-chloro-benzoyl)-L-tyrosine instead of O,N-(di-benzoyl)-L-tyrosine and using di-n-butylamine instead of di-n-propylamine.

Yield 74%. Melting point 113°–116°. (Crystallised by ethanol).

EXAMPLE 82

N-(o-chloro-benzoyl)-DL-tyrosil-di-n-butylamide

Procedure as in Example 3.

Yield 89%. Melting point 151°–153°. (Crystallised by ethanol).

EXAMPLE 83 (CR 731)

O-[3-(N''-methyl-piperazine)-N'-propyl]-N-(o-chloro-benzoyl)-DL-tyrosil-di-n-butylamide Procedure as in Example 4, using N-(o-chloro-benzoyl)-DL-tyrosil-di-n-butylamide instead of N-benzoyl-DL-tyrosil-di-n-propylamide and using N-2-chloroethyl-N'-methyl-piperazine instead of 2-diethylamino-ethyl-chloride.

Finally the oily base is directly converted into citrate.

Yield 69%. Melting point (citrate): 109°–111°. (Crystallised by acetone).

EXAMPLE 84

O,N-(di-p-bromobenzoyl)-tyrosine

Procedure as in Example 1, using p-bromo-benzoyle-chloride instead of benzoyle chloride.

Yield 80%. Melting point 210°–213°. (Crystallised by ethanol). $(\alpha)_D^{20} = +3\pm2$ in tetrahydrofurane).

EXAMPLE 85

O,N-(di-p-bromobenzoyl)-DL-tyrosil-di-n-propylamide

Procedure as in Example 2, using O,N-di-(p-bromobenzoyl)-L-tyrosine instead of O,N-di-benzoyl-L-tyrosine.

Yield 75%. Melting point 161°–163°. (Crystallised by methanol).

EXAMPLE 86

N-(p-bromo-benzoyl)-DL-tyrosil-di-n-propylamide

Procedure as in Example 3.

Yield 88%. Melting point 207°–210°. (Crystallised by methanol).

EXAMPLE 87 (CR 631)

O-(2-diethylamino-ethyl)-N-(p-bromobenzoyl)-DL-tyrosil-din-propylamide

Procedure as in Example 4, using N-(p-bromobenzoyl)-DL-tyrosil-di-n-propylamide instead of N-benzoyl-DL-tyrosil-di-n-propylamide.

Finally the solid base is obtained by recrystallisation with ethyl acetate.

Yield 78%. Melting point (base): 118°–120°.

EXAMPLE 88

O,N-(di-p-nitrobenzoyl)-L-tyrosine

Procedure as in Example 1, using p-nitrobenzoyl chloride instead of benzoyl chloride.

Yield 77%. Melting point 205°–210°. (Crystallised by ethanol-$H_2O$). $(\alpha)_D^{20} = -10\pm2$ (in tetrahydrofurane.)

EXAMPLE 89

O,N-(di-p-nitrobenzoyl)-DL-tyrosil-di-n-propylamide

Procedure as in Example 2, using O,N-(di-p-nitrobenzoyl)-L-tyrosine instead of O,N-(di-benzoyl)-L-tyrosine.

Yield 74%. Melting point 136°–140°. (Crystallised by ethanol.)

EXAMPLE 90

N-(p-nitrobenzoyl)-DL-tyrosil-di-n-propylamide

Procedure as in Example 3.

Yield 90%. Melting point 193°–195°. (Crystallised by ethanol).

EXAMPLE 91 (CR 620)

O-(2-dimethylamino-ethyl)-N-(p-nitro-benzoyl)DL-tyrosil-di-n-propylamide

Procedure as in Example 4, using N-(p-nitrobenzoyl)-DL-tyrosil-di-n-propylamide instead of N-benzoyl-DL-tyrosil-di-n-propylamide and using 2-dimethylamino-ethylchloride instead of 2-diethylamino-ethyl-chloride.

Finally the oily base is directly converted into oxalate.

Yield 80%. Melting point (oxalate): 136°–138°. (Crystallised by acetone.)

EXAMPLE 92

O,N-[di-p-trifluoro-methyl)-benzoyl]-L-tyrosine

Procedure as in Example 1, using p-(trifluoromethyl)-benzoyl-chloride instead of benzoyl-chloride Yield 79%. Melting point 187°–190°. (Crystallised by ethanol). $(\alpha)_D^{20} = +16\pm2$ (in tetrahydrofurane).

EXAMPLE 93

O,N-[di-p-trifluoro-methyl)-benzoyl]-DL-tyrosil-di-n-propylamide

Procedure as in Example 2, using O,N-di-p-(trifluoromethyl)-benzoyl-L-tyrosine instead of O,N-dibenzoyl-L-tyrosine.

Yield 76%. Melting point 180°–184°. (Crystallised by ethanol).

EXAMPLE 94

N-[p-(trifluoro-methyl)-benzoyl]-DL-tyrosil-di-n-propylamide

Procedure as in Example 3.

Yield 90%. Melting point 203°–206°. (Crystallised by ethanol).

EXAMPLE 95 (CR 635)

O-(2-diethylamino-ethyl)-N-[p-(trifluoro-methyl)-benzoyl]-DL-tyrosil-di-n-propylamide Procedure as in Example 4, using N-[p(trifluoromethyl)-benzoyl]-DL-tyrosil-di-n-propylamide instead of N-benzoylDL-tyrosil-di-n-propylamide.

Finally the oily base is directly converted into oxalate.

Yield 79%. Melting point (oxalate): 190°–193°. (Crystallised by acetone-ethanol).

EXAMPLE 96

O,N-di-(p-methoxy-benzoyl)-L-tyrosine

Procedure as in Example 1, using di-p-metoxy-benzoyl-chloride instead of benzoyl-chloride.

Yield 71%. Melting point 171°–174°. (Crystallised by methanol). $(\alpha)_D^{20} = +20\pm2$ (in tetrahydrofurane.)

EXAMPLE 97

O,N-(di-p-metoxy-benzoyl)-DL-tyrosil-di-n-propylamide

Procedure as in Example 2, using O,N-(di-p-metoxybenzoyl)-L-tyrosine instead of O,N-(di-benzoyl)-L-tyrosine.

Yield 68%. Melting point 66°–72°. Amorphous substance.

EXAMPLE 98

N-(p-metoxy-benzoyl)-DL-tyrosil-di-n-propylamide

Procedure as in Example 3.

Yield 87%. Melting point 121°–124°. (Crystallised by ethanol).

EXAMPLE 99 (CR 644)

O-(2-diethylamino-ethyl)-N-(p-metoxy-benzoyl)-DL-tyrosil-di-n-propylamide

Procedure as in Example 4, using N-(p-metoxy-benzoyl)-DL-tyrosil-di-n-propylamide instead of N-benzoyl-DL-tyrosil-di-n-propylamide.

Finally the oily base is directly converted into oxalate.

Yield 74%. Melting point 112°–115°. (Crystallised by acetone).

EXAMPLE 100

O,N-(3,4-di-methyl-benzoyl)-L-tyrosine

Procedure as in Example 1, using 3,4-di-methyl-benzoylchloride instead of benzoyl-chloride.

Yield 73%. Melting point 206°–209°. (Crystallised by ethanol 95%). $(\alpha)_D^{20} = 22,5\pm2$ (in tetrahydrofurane).

EXAMPLE 101

O,N-(di-3,4-di-methyl-benzoyl)-DL-tyrosil-di-n-propylamide

Procedure as in Example 2, using O,N-(di-3,4-dimethylbenzoyl)-L-tyrosine instead of O,N-(di-benzoyl)-L-tyrosine.

Yield 70%. Melting point 174°–178°.

EXAMPLE 102

N-(3,4-di-methyl-benzoyl)-DL-tyrosil-di-n-propylamide

Procedure as in Example 3.

Yield 88%. Melting point 190°–192°. (Crystallised by ethanol 95%).

EXAMPLE 103 (CR 632)

O-(2-diethylamino-ethyl)-N-(3,4-di-methyl-benzoyl)-DL-tyrosil-di-n-propylamide.

Procedure as in Example 4, using N-(3,4-dimethylbenzoyl)-DL-tyrosil-di-n-propylamide instead of N-benzoylDL-tyrosil-di-n-propylamide.

Finally the oily base is directly converted into oxalate.

Yield 76%. Melting point (oxalate): 168°–171°. (Crystallised by acetone).

EXAMPLE 104

O,N-(di-carbobenzoxy)-L-tyrosine

Procedure as in Example 1, using carbobenzoxy-chloride instead of benzoyl-chloride.

Yield 78%. Melting point 86°–87°. (Crystallised by carbon tetrachloride). $(\alpha)_D^{20} = +21\pm2$ (in tetrahydrofurane).

EXAMPLE 105

O,N-(di-carbobenzoxy)-L-tyrosil-di-n-propylamide

Procedure as in Example 2, using O,N-(di-carbobenzoxy)-L-tyrosine instead of O,N-(di-benzoyl)-L-tyrosine.

Yield 78%.

A non-crystallising oil.

EXAMPLE 106

N- carbobenzoxy-L-tyrosil-di-n-propylamide

Procedure as in Example 3.

Yield 86%. Melting point 138°–140°. (Crystallised by ethanol 95%). $(\alpha)_D^{20} = -6\pm2$ (in tetrahydrofurane).

EXAMPLE 107 (CR 603)

O-(2-dimethylamino-ethyl)-N-carbobenzoxy-L-tyrosil-di-n-propylamide

Procedure as in Example 4, using N-carbobenzoxy-L-tyrosil-di-n-propylamide instead of N-benzoyl-DL-tyrosildi-n-propylamide and using 2-dimethylamino-ethylchloride instead of 2-diethylamino-ethylchloride.

Finally the oily base is directly converted into oxalate.

Yield 74%. Melting point (oxalate): 100°–102°. (Crystallised by acetone-ether). $(\alpha)_D^{20} = +11\pm2$ (in H$_2$O).

EXAMPLE 108 (CR 830)

O-(2-diethylamino-ethyl)-N-carbobenzoxy-L-tyrosil-di-n-propylamide

Procedure as in Example 4, using N-carbobenzoxy-L-tyrosil-di-n-propylamide instead of N-benzoyl-DL-tyrosil-di-n-propylamide.

Finally the oily base is directly converted into oxalate.

Yield 70%. Melting point (oxalate): 87°–90°. (Crystallised by acetone-ether). $(60)_D^{20} = +8\pm2$ (in H$_2$O).

EXAMPLE 109

O,N-(carbobenzoxy)-L-tyrosil-morpholylamide

Procedure as in Example 2, using O,N-(di-carbobenzoxy)-L-tyrosine instead of O,N-(di-benzoyl)-L-tyrosine and using morpholine instead of di-n-propylamine.

Yield 79%

A non-crystallising oil.

EXAMPLE 110

N-carbobenzoxy-L-tyrosil-morpholylamide

Procedure as in Example 3.

Yield 82%. Melting point 65°–76°. (Amorphous substance). $(\alpha)_D^{20} = -6\pm2$ (in tetrahydrofurane).

EXAMPLE 111 (CR 606)

O-(2-dimethylamino-ethyl)-N-carbobenzoxy-L-tyrosil-morpholylamide

Procedure as in Example 4, using N-carbobenzoxy-L-tyrosil-morpholilamide instead of N-benzoyl-DL-tyrosil-di-n-propylamide and using 2-dimethylamino-ethylchloride instead of 2-diethylamino-ethylchloride.

Finally the oily base is directly converted into oxalate.

Yield 71%. Melting point (oxalate): 85°–86°. (Crystallised by acetone). $(\alpha)_D^{20} = +4\pm2$ (in tetrahydrofurane).

EXAMPLE 112

O,N-(di-carbobenzoxy)-L-tyrosil-ethylamide

Procedure as in Example 2, using O,N(di-carbobenzoxy)-L-tyrosine instead of O,N-(di-benzoyl)-L-tyrosine and using ethylamine instead of di-n-propylamine.

Yield 72%. Melting point 189°–191°. $(\alpha)_D^{20} = +5\pm2$ (in tetrahydrofurane).

EXAMPLE 113

N-(carbobenzoxy)-L-tyrosil-ethylamide

Procedure as in Example 3.

Yield 84%. Melting point 152°–154°. (Crystallised by ethanol — H$_2$O). $(\alpha)_D^{20} = +7\pm2$ (in tetrahydrofurane).

EXAMPLE 114 (CR 610)

O-(2-dimethylamino-ethyl)-N-carbobenzoxy-L-tyrosil-ethylamide

Procedure as in Example 4, using N-(carbobenzoxy)-L-tyrosil-ethylamide instead of N-benzoyl-DL-tyrosil-di-n-propylamide, and using 2-dimethylamino-ethylchloride instead of 2-diethylamino-ethylchloride.

Finally the oily base is directly converted into oxalate.

Yield 73%. Melting point (oxalate): 98°–100°. (Crystallised by acetone). $(\alpha)_D^{20} = +10\pm2$ (in H$_2$O).

EXAMPLE 115

O,N-(di-carbobenzoxy)-L-tyrosil-benzylamide

Procedure as in Example 2, using O,N-(di-carbobenzoxy)-L-tyrosine instead of O,N-(di-benzoyl)-L-tyrosine and using benzylamine instead of di-n-propylamine.

Yield 76%. Melting point 184°–188°. $(\alpha)_D^{20} = +1\pm2$ (in tetrahydrofurane).

EXAMPLE 116

N-carbobenzoxy-L-tyrosil-benzylamide

Procedure as in Example 3.

Yield 88%. Melting point 157°–160°. (Crystallised by ethanol). $(\alpha)_D^{20} = +3\pm2$ (in tetrahydrofurane).

EXAMPLE 117 (CR 612)

O-(2-dimethylamino-ethyl)-N-carbobenzoxy-L-tyrosil-benzylamide

Procedure as in Example 4, using N-carbobenzoxy-L-tyrosil-benzylamide instead of N-benzoyl-DL-tyrosil-di-n-propylamide and using 2-dimethylamino-ethyl-chloride instead of 2-diethylamino-ethylchloride.

Finally the oily base is directly converted into chlorohydrate.

Yield 71%. Melting point (chlorohydrate): 205°–208°. (Crystallised by ethanol). $(\alpha)_D^{20} = +6\pm2$ (in $H_2O$).

EXAMPLE 118

O,N-(di-p-nitro-carbobenzoxy)-L-tyrosine

Procedure as in Example 1, using p-nitro-carbobenzoxy chloride instead of benzoyl-chloride.

Yield 73%. Melting point 150°–153°. (Crystallised by ethanol — $H_2O$). $(\alpha)_D^{20} = +10\pm2$ (in tetrahydrofurane).

EXAMPLE 119

O,N-(di-p-nitro-carbobenzoxy)-L-tyrosil-di-n-propylamide

Procedure as in Example 2, using O,N-(di-p-nitrocarbobenzoxy)-L-tyrosine instead of O,N-(di-benzoyl)-L-tyrosine.

Yield 77%.

A non-crystallising oil.

EXAMPLE 120

N-(p-nitro-carbobenzoxy)-L-tyrosil-di-n-propylamide

Procedure as in Example 3.

Yield 84%. Melting point 160°–163°. (Crystallised by ethanol 95%). $(\alpha)_D^{20} = -4\pm2$ (in tetrahydrofurane).

EXAMPLE 121 (CR 613)

O-(2-dimethylamino-ethyl)-N-p-nitro-carbobenzoxy)-L-tyrosil-di-n-propylamide

Procedure as in Example 4, using N-(p-nitrocarbobenzoxy)-L-tyrosil-di-n-propylamide instead of N-benzoylDL-tyrosil-di-n-propylamide and using 2-dimethylaminoethylchloride instead of 2-diethylamino-ethylchloride.

Yield 70%. Melting point 124°–127°. (Crystallised by acetone). $(\alpha)_D^{20} = +5\pm2$ (in $H_2O$).

EXAMPLE 122

O,N-(di-carbobenzoxy)-DL-tyrosine

Procedure as in Example 1, using DL-tyrosine instead of L-tyrosine and using carbobenzoxy-chloride instead of benzoyl-chloride.

Yield 81%. Melting point 144°–146°. (Crystallised by ethanol 95%).

EXAMPLE 123

O,N-(di-carbobenzoxy)-DL-tyrosil-di-n-propylamide

Procedure as in Example 2, using O,N-(di-carbobenzoxy)-DL-tyrosine instead of O,N-(di-benzoyl)-L-tyrosine.

Yield 77%. Melting point 83°–85°. (Crystallised by ethanol 95%).

EXAMPLE 124

N-carbobenzoxy-DL-tyrosil-di-n-propylamide

Procedure as in Example 3.

Yield 87%. Melting point 104°–106°. (Crystallised by ethanol 95%).

EXAMPLE 125 (CR 832)

O-(2-diethylamino-ethyl)-N-carbobenzoxy-DL-tyrosil-di-n-propylamide

Procedure as in Example 4, using N-carbonbenzoxy-DL-tyrosil-di-n-propylamide instead of N-benzoyl-DL-tyrosildi-n-propylamide.

Finally the oily base is directly converted into oxalate.

Yield 76%. Melting point (oxalate): 148°–150°. (Crystallised by ethanol).

EXAMPLE 126

O,N-(di-carbobenzoxy)-D-tyrosine

Procedure as in Example 1, using D-tyrosine instead of L-tyrosine, and using carbobenzoxy-chloride instead of benzoyl-chloride.

Yield 78%. Melting point 83°–86°. (Crystallised by carbon tetrachloride). $(\alpha)_D^{20} = -16\pm2$ (in tetrahydrofurane).

EXAMPLE 127

O,N-(di-carbobenzoxy)-D-tyrosil-di-n-propylamide

Procedure as in Example 2, using O,N-(di-carbobenzoxy)-D-tyrosine instead of O,N-(di-benzoyl)-L-tyrosine.

Yield 71%.

A non-crystallising oil.

EXAMPLE 128

N-carbobenzoxy-D-tyrosil-di-n-propylamide

Procedure as in Example 3.

Yield 86%. Melting point 129°–133°. (Crystallised by ethanol — $H_2O$). $(\alpha)_D^{20} = +5\pm2$ (in tetrahydrofurane).

EXAMPLE 129 (CR 627)

O-(2-diethylamino-ethyl)-N-carbobenzoxy-D-tyrosil-di-n-propylamide

Procedure as in Example 4, using N-carbobenzoxy-D-tyrosildi-n-propylamide instead of N-benzoyl-DL-tyrosil-di-n-propylamide.

Finally the oily base is directly converted into oxalate.

Yield 72%. Melting point (oxalate): 90°–93°. $(\alpha)_D^{20} = -7\pm2$ (in tetrahydrofurane).

EXAMPLE 130

L-tyrosil-di-n-propylamide 39.8 g (0.1 moles) of N-carbobenzoxy-L-tyrosil-di-n-propylamide are dissolved in 400 cc of methanol and 100 cc of H$_2$O. There are added 4 g of carbon supported palladium at 10% and then hydrogen is bubbled through the solution for six hours, under agitation. At this point the catalyst is filtered off and the solvent is evaporated; the residue obtained is poured into 200 cc of H$_2$O. This quickly forms a crystalline precipitate which is filtered, and recrystallised by ethanol-H$_2$O Yield 92%. Melting point 108°–110°. $(\alpha)_D^{20} = +70\pm2$ (in tetrahydrofurane).

EXAMPLE 131

N-benzoyl-L-tyrosil-di-n-propylamide

To a solution of 248 g (0.1 moles) of L-tyrosil-di-n-propylamide dissolved in 300 cc of chloroform is added, contemporaneously, under agitation in about 30' and keeping the temperature of the reaction between 5° and 10°, 100 cc of NaOH1N and 14.05 g (0.1 moles) of benzoylchloride. This is maintained in agitation for 12 hours. The organic phase is extracted twice with HCl 2 N, washed with water until the reaction is neutralised, anhydrified on CaCl$_2$ and concentrated to small volume. By addition of petroleum ether the product is precipitated.

Yield 89%. Melting point 192°–193°. (Crystallised by ethanol). $(\alpha)_D^{20} = -27,5\pm2$ (in tetrahydrofurane).

EXAMPLE 132 (CR 804)

O-(2-diethylamino-ethyl)-N-benzoyl-L-tyrosil-di-n-propylamide

Procedure as in Example 4, using N-benzoyl-L-tyrosildi-n-propylamide instead of N-benzoyl-DL-tyrosil-di-n-propylamide.

Finally the oily base is directly converted into oxalate.

Yield 80%. Melting point (oxalate): 82°–85°. (Crystallised by acetone-ether). $(\alpha)_D^{20} = -17\pm2$ (in H$_2$O).

EXAMPLE 133

N-(p-chloro-benzoyl)-L-tyrosil-di-n-promylamide

Procedure as in Example 130, using p-chloro-benzoylchloride instead of benzoyl-chloride.

Yield 86%. Melting point 199°–202°. (Crystallised by ethanol). $(\alpha)_D^{20} = -12\pm2$ (in tetrahydrofurane).

EXAMPLE 134 (CR 831)

O-(2-diethylamino-ethyl)-N-(p-chloro-benzoyl)-L-tyrosil-din-propylamide

Procedure as in Example 4, using N-(p-chloro-benzoyl)-L-tyrosil-di-n-propylamide instead of N-benzoyl-DL-tyrosildi-n-propylamide.

Finally the oily base is directly converted into oxalate.

Yield 79%. Melting point (oxalate): 89°–92°. (Crystallised by acetone-ether). $(\alpha)_D^{20} = -10\pm2$ (in H$_2$O).

The antispastic activity of the compounds of this invention is exhibited at the peripheral smooth muscle level with an action mechanism which resembles, while differing from it partially, that which is traditionally defined as the papaverine type.

By choosing as comparison substance papaverine, a drug at present widely used in human therapy for spastic syndromes, one can see from Table 1 that most of the products of this invention have an antispastic activity one or two times greater than that of papaverine according to the substance and the test being considered.

In this table (n. 1) there are recorded the compounds described in the examples with their relative serial numbers, the acute toxicity, the antispastic activity observed in two experimental tests, one "in vivo" and one "in vitro". There are moreover recorded two therapeutic indices which take account of the toxicity of these compounds in relation to their in vivo and in vitro activity. More precisely:

A. DL$_{50}$ which, as is known, is the quantity of the substance expressed in mg/kg of animal weight, capable of causing death in 50% of the animals treated.

B. The vegetable carbon method in vivo (charcoal method) which consists of administering by oral means to rats, which have fasted for 24 hours, 0.3ml/per rate of a mixture consisting of: 10g of charcoal and 5 g of gum arabic suspended in a volume of 100 cc of H$_2$O as well as at the same time the substance being studied, accordingly as desired, generally i.v., s.c., oral. After two hours the animals are killed and those are taken to be negative in which the charcoal has reached the first portion of the colon and the others positive, in the sense that the substance administered has slowed down the intestinal transit of the charcoal.

In effect the animals treated with a physiological solution (checks) are all negative after two hours.

C. The method in vitro is that of Magnus, with the ileum of the cavy, and is in common use for all evaluations. It consists of extracting the ileum from the cavy and placing it in a receptacle which contains nutritive liquid, suitably oxygenated, and registering the movements of the organ which remains alive for several hours if maintained at a temperature of 37°. According to the traditional method followed by us, BaCl$_2$ is put into the bath as a spasmisant: the reaction is a violent contraction of the organ. This contraction can be prevented by adding beforehand pharmaceuticals which inhibit spasms, and in this case our compounds.

The values recorded are expressed as relation between papaverine and the ED$_{50}$ of our compounds. (As is known, the ED$_{50}$ is the dose which results in a 50% reduction in spastic contraction).

D. I.T.$_1$ is the therapeutic index under the profile of the antispastic activity in vivo, and it is obtained by recording the DL$_{50}$ (column 2) with the ED$_{50}$ of the charcoal test (column 3).

E. I.T.$_2$ is the therapeutic index under the profile of the antispastic activity in vitro and is given by the product between the in vitro antispastic activity index (column 4) and the corresponding DL$_{50}$ (column 2).

TABLE 1

ANTISPASTIC ACTIVITY IN VIVO AND IN VITRO OF THE COMPOUNDS AND THEIR RELATIVE THERAPEUTICAL INDICES

| 1 COMPOUNDS | 2 $DL_{50}$ in a rat mg/kg i.v. | 3 Antisp. activity in transit test: $ED_{50}$ mg/kg i.v. | 4 Antisp. activity in vitro on the ileum of a cavy by Stim. BaCl $ED_{50}$ pap.$^2$/$ED_{50}$CR | 5 I.T.1: $DL_{50}/ED_{50}$ in vivo | 6 I.T.2: $DI_{50}$CR $ED_{50}$pap. $ED_{50}$CR |
|---|---|---|---|---|---|
| Ex. 4 (CR 605) | 33.9 | 10.6 | 1.25 | 3.2 | 42.5 |
| Ex. 5 (CR 592) | 58.1 | 47.5 | 0.25 | 1.2 | 14.0 |
| Ex. 6 (CR 624) | 24.4 | inactive | 1.12 | — | 27.5 |
| Ex. 7 (CR 823) | 23.0 | 16.2 | 1.48 | 1.4 | 34.1 |
| Ex. 8 (CR 816) | 16.0 | 5.5 | 2.00 | 2.9 | 32.0 |
| Ex. 9 (CR 829) | 20.1 | 15.2 | — | 1.3 | — |
| Ex.10 (CR 607) | 32.4 | 26.7 | 0.41 | 1.2 | 13.3 |
| Ex.11 (CR 625) | 32.6 | 21.1 | 0.52 | 1.5 | 16.9 |
| Ex.12 (CR 630) | 36.1 | 40.1 | — | 0.9 | — |
| Ex.13 (CR 609) | 138.7 | 50.5 | 0.68 | 2.7 | 94.0 |
| Ex.14 (CR 619) | 110.2 | 67.8 | — | 1.6 | — |
| Ex.15 (CR 700) | 19.3 | 20.4 | — | 0.95 | — |
| Ex.18 (CR 740) | 102 | inactive | 0.36 | — | 36.4 |
| Ex.21 (CR 738) | 85.3 | 50.6 | 0.14 | 1.7 | 11.9 |
| Ex.24 (CR 608) | 162 | 104.3 | — | 1.5 | — |
| Ex.25 (CR 711) | 82 | inactive | 0.42 | — | 34.4 |
| Ex.28 (CR 821) | 53 | 15.6 | 0.13 | 3.4 | 6.9 |
| Ex.31 (CR 734) | 62.2 | 33.4 | 0.52 | 1.8 | 32.3 |
| Ex.32 (CR 736) | 102.0 | 39.6 | 0.04 | 2.5 | 4.0 |
| Ex.35 (CR 648) | 35.6 | 10.7 | 0.16 | 3.3 | 5.7 |
| Ex.36 (CR 702) | 81.4 | 62.5 | 0.11 | 1.3 | 9.0 |
| Ex.37 (CR 786) | 38.0 | 34.3 | 0.17 | 1.1 | 6.5 |
| Ex.40 (CR 825) | 42.0 | 14.8 | 1.8 | 2.8 | 75.7 |
| Ex.43 (CR 616) | 73.6 | inactive | 0.82 | — | 60.0 |
| Ex.46 (CR 614) | 58.7 | 53.2 | — | 1.1 | — |
| Ex.49 (CR 611) | 108.5 | 59.8 | — | 1.8 | — |
| Ex.53 (CR 615) | 48.1 | inactive | 0.69 | — | 33.2 |
| Ex.54 (CR 650) | 17.5 | 18.4 | 1.17 | 0.95 | 20.5 |
| Ex.55 (CR 807) | 31.5 | 21 | 0.34 | 1.5 | 10.7 |
| Ex.58 (CR 651) | 34.1 | 16.3 | 1.60 | 2.1 | 55.0 |
| Ex.59 (CR 797) | 20.6 | 12.0 | 1.32 | 1.7 | 27.2 |
| Ex.60 (CR 709) | 40 | 36.1 | — | 1.1 | — |
| Ex.63 (CR 826) | 41 | 17.0 | 1.2 | 2.4 | 49.2 |
| Ex.67 (CR 716) | 56.4 | 26.5 | 1.58 | 2.1 | 89.1 |
| Ex.68 (CR 725) | 62.6 | 12.2 | 3.20 | 5.1 | 200 |
| Ex.69 (CR 727) | 26.3 | 24.9 | 1.52 | 1.05 | 40 |
| Ex.70 (CR 733) | 43.5 | 16.7 | 1.31 | 2.6 | 57 |
| Ex.73 (CR 714) | 111 | inactive | 0.42 | — | 34.4 |
| Ex.76 (CR 705) | 80 | 31 | 1.57 | 2.1 | 126 |
| Ex.77 (CR 729) | 38.6 | 23 | 2.45 | 1.6 | 94.6 |
| Ex.78 (CR 730) | 50 | 30.2 | 0.99 | 1.6 | 49.5 |
| Ex.79 (CR 812) | 27 | 21 | 1.03 | 1.3 | 27.8 |
| Ex.83 (CR 731) | 61 | 39.4 | 1.75 | 1.5 | 106.7 |
| Ex.87 (CR 631) | 60.2 | 40.4 | 1.22 | 1.5 | 73.1 |
| Ex.91 (CR 620) | 116.7 | inactive | 0.36 | — | 41.8 |
| Ex.95 (CR 635) | 38.7 | 25.6 | 0.95 | 1.5 | 36.8 |
| Ex.99 (CR 644) | 56.4 | 20.2 | 0.45 | 2.8 | 25.3 |
| Ex.103 (CR 632) | 38.1 | 26.0 | 0.40 | 1.4 | 15.2 |
| Ex.107 (CR 603) | 63.0 | 30.5 | 2.40 | 2.05 | 151 |
| Ex.108 (CR 830) | 31.5 | 17.3 | 1.49 | 1.8 | 47.2 |
| Ex.111 (CR 606) | 127.8 | inactive | 0.19 | — | 24.3 |
| Ex.114 (CR 610) | 139.4 | 58.1 | 0.13 | 2.4 | 18.2 |
| Ex.117 (CR 612) | 87.7 | 23.0 | 0.35 | 3.8 | 30.5 |
| Ex.121 (CR 613) | 100.4 | 58.7 | 0.68 | 1.7 | 68.2 |
| Ex.125 (CR 832) | 32.4 | 16.3 | 1.40 | 1.9 | 45.3 |
| Ex.129 (CR 627) | 34.0 | 20.8 | 1.44 | 1.6 | 48.9 |
| Ex.132 (CR 804) | 33.5 | 16.1 | 0.89 | 2.1 | 29.8 |
| Ex.134 (CR 831) | 35.0 | 24.4 | 1.30 | 1.4 | 45.5 |
| Papaverina | 27.2 | 22.5 | 1 | 1.2 | 27.2 |

Examination of this table makes it apparent that the majority of compounds under consideration have at least one of the following advantages compared with papaverine.

1. greater activity
2. the therapeutic indices are more favourable, i.e. compared with papaverine these compounds are more active and less toxic.

The activities which have been described so far both in vitro and in vivo can be confirmed using different animals or different organs. These activities are further improved if, instead of BaCl₂ other spasmisers are used, such as serotoninehistamine and oxytocine (see Table 2).

This broad evaluation is especially indicated for the characteristics of the compounds of our invention so as to give an idea of how they are able to act upon different components of the spasms of smooth muscles in vivo.

Examination of this table in fact makes it apparent that these compounds are not only active with papaverine type mechanism, but it also shows how they are able to inhibit, in varying degree, the spasmodic activity of serotonin histamine and oxytocine.

Thus for example the antiserotoninic activity is at levels similar to those of methysergide (a pharmaceutical well known as one of the most powerful antiserotoninics), whilst the antihistaminic is little inferior to that of prometazine (pharmaceutical used as an antihistaminic).

One applicable aspect of these characteristics is exactly that of their use in the painful spasms of humans, which respond to different physiological causes, since sometimes, hormonal situations can be involved (analogous with a spasm with $BaCl_2$), or else endogenous liberation of histamine or of serotonine.)

It is particularly interesting to note that specially in vivo the compounds described in this invention are indirectly more active than papaverine.

This activity is much more interesting if one considers that the anticolinergics such as atropine and Joscina-N-butyl-bromide (pharmaceuticals widely used in therapy for spastic forms) are inactive to these tests.

Another interesting characteristic of these com-

TABLE 2

Antispastic activity in vitro on cavy ileum, rat uterus

| Substances | Cavy ileum | | | Rat Uterus |
|---|---|---|---|---|
| | $BaCl_2$ | Serotonine | Istamine | Oxytocine |
| CR 605 | 1.25 | 0.69 | 0.17 | 0.09 |
| CR 725 | 3.20 | 1.2 | 0.24 | 0.18 |
| CR 716 | 1.58 | 0.74 | 0.08 | 0.06 |
| CR 603 | 2.4 | 0.87 | 0.09 | 0.008 |
| Papaverine | -1- $(1.29.10^{-8})$ | — | — | -1- $(26.607.10^{-9})$ |
| Methysergide | — | -1- $(0.49.10^{-9})$ | — | — |
| Prometazine | — | — | -1- $(1.758)$ | — |

The values contained in the table are expressed as comparison between the $ED_{50}$ of the substance test made, equal to 1 and the $ED_{50}$ of the substance being studied, and they therefore express the activity of the compounds compared with known, very active substances.

Another aspect of the antispastic activity of these compounds is that which can be obtained both in vivo and in vitro on the urinary tracts (ureter) and on the bladder.

The in vivo evaluation was made upon the urinary bladder of a rat anaesthetised and placed in an environment heated to the animals body temperature whilst the bladder which is exposed is linked to a system which registers its movement. The pharmaceutilcals were given to the animals by intravenous means.

The in vitro evaluation was made on a rat's ureter suspended in a bath of physiological liquid according to a method similar to the Magnus method already described.

In Table 3 a few examples of this activity are given.

TABLE 3

| Substances | Urinary sac of rat in "vivo" $ED_{50}$mg/kg in "vivo" | Ureter of rat in "vitro" $ED_{50}\mu g/ml$ in "vitro" |
|---|---|---|
| CR 605 | 6.25 | 74.2 |
| CR 725 | 8.32 | 27.3 |
| CR 603 | 6.90 | 86 |
| Atropine | — | inactive |
| Joscina Butyl-bromide | inactive | — |
| Papaverine | 7.59 | 45.2 | pounds is that they do not generally disturb the physiological rhythm of the organs upon which they are acting, whereas on the contrary they act energetically when these organs undergo spasm.

The results given in Table 4 are particular significant in this respect.

TABLE 4

Activity of the compounds upon the gastro-pyloric and bile duct spasm

| | | STOMACH AND PYLORUS | | | BILE DUCTS | | |
|---|---|---|---|---|---|---|---|
| SUBSTANCES | | After the 1st hour | After the 2nd hour | %age variation between 1st | After the 1st hour | After the 2nd hour | %age variation between the 1st and |
| n° | mg/kg | (ml) | (ml) | and 2nd hour | (ml) | (ml) | 2nd hour |
| Checks | Physiological sol. | 185.2 | 153.7 | −17 | 41.7 | 38.5 | − 8.6 |
| Morphine | 250 µg | 213.1 | 96.9 | −54.5 | 49.5 | 25.6 | −48.3 |
| CR 605 | 5 | 131.2 | 132.9 | + 1.2 | 46.6 | 56.6 | +21.5 |
| Morphine + CR 605 | 250 µg + 5 | 171.3 | 186.6 | + 8.9 | 50.8 | 58.3 | +14.9 |
| CR 725 | 10 | 167.2 | 165.5 | − 1.0 | 49.7 | 53.2 | + 7.2 |
| Morphine + CR 725 | 250 µg + 10 | 187.6 | 191.2 | + 1.9 | 47.2 | 51.0 | +10.8 |
| CR 603 | 12.5 | 157.0 | 160.8 | + 2.4 | 50.3 | 48.8 | − 3.0 |
| Morphine + CR 603 | 250 µg + 12.5 | 147.6 | 154.3 | + 4.5 | 44.0 | 39.5 | −10.2 |

The results shown in this table were obtained by perfusing with a physiological solution, the stomach and the bile ducts respectively and collecting the liquid emerging after the pylorus and the sphineter of Oddi. It can be noted that there are no significant flux variations between the first and second hours of collection.

If the compounds of this invention are administered intravenously, some of which compounds are precisly exemplified in Table 4, no significant variations occur in the outflow of liquid; however, if, immediately after the first hour of collection one administers the indicated dose of morphine, then there is a strong reduction of flow in the second hour, which is evidence of a spasm situation of the ducts leading to the sphincter.

When our compounds are administered at the same time as morphine and with the indicated doses, they nullify the said spasm.

This characteristic, which is peculiar to these compounds, takes on a special importance under the therapeutic profile, since it indicates that the said compounds are active only in the presence of a pathological component, leaving the normal functioning of the organism undisturbed.

These compounds are also active in reducing spasms in the smooth muscles of the blood vessels. In a few of these the said activity is of such interest as to be able to be used therapeutically.

An in vitro evaluation of this activity was made upon the caudal artery of a rat, suspended, so that one can register the variation of internal pressure, and contracted with ergotamine tartrate put in to the arterial lumen of the said vessel with a dose of 350 µg/ml of perfusion liquid.

The spasm was antagonised with the compounds being tested. The evaluation was made with $ED_{50}$, i.e., a concentration of the product in the perfusion liquid expressed as µg/ml able to reduce the contraction thus induced by 50%.

In Table 5 a few examples of this activity are given.

TABLE 5

Antispastic activity of some of the claimed compounds upon the caudal artery of a rat stimulated with ergotamine tartrate: values are expressed in $ED_{50}$ (see specification).

| Substance | $ED_{50}$ µg/ml |
|---|---|
| CR 603 | 105 |
| CR 651 | 37 |
| CR 816 | 12 |

In another experiment the caudal artery of a rat was electrically stimulated and the pharmaceuticals were added to the bath. The activity was assessed at $ED_{50}$, i.e., the quantity of pharmaceutical expressed in µg/ml of the perfusion liquid able to reduce by half the response of the electric stimulation compared with that of the checks.

TABLE 6

Antispastic activity of some of the compounds claimed on the caudal artery of a rat, electrically stimulated: the values are expressed in $ED_{50}$ (see Specification).

| Substance | $ED_{50}$ µg/ml |
|---|---|
| CR 603 | 76 |
| CR 651 | 19 |
| CR 816 | 7 |

THERAPEUTIC USE AND PHARMACEUTICAL FORMS

For use in human beings the compounds of the invention can be made up in oral and parenteral pharmaceutical forms, consisting of the compound alone or with acceptable pharmaceutical excipients. For example, for the compound CR 605 the following pharmaceutical forms are possible, among others:

a. Phial for intravenal use by 5 to 10 ml containing 50 mg of compound plus physiological solution q.b. respectively at 5 or 10 ml. These phials can be used in quantity varying from one to three daily.

b. Phial for intramuscular use by 3 ml containing 30 mg of compound plus physiological solution q.b. to 3 ml. The recommended dosage is the same as that for the phial for intravenal use.

c. Tablets containing 100 mg of compound, obtained by compression of the powder admixed with pharmaceutically acceptable excipients, such for example as: amido, lactose, talc, magnesium stearate, etc. The minimum recommended dosage is 3 compresses per diem which, in cases needing it, can be doubled.

d. Suppositories containing 200 mg of compound combined with pharmaceutically acceptable excipients. These suppositories can be given from one to three per diem accordingly as required.

Similar pharmaceutical forms with dosages varying in accordance with the therapeutic indices are envisaged for the other compounds.

Tolerance in animals and human beings, as well as chronic toxicity in the animals, show no negative aspects with these compounds.

Therapeutic use of the pharmaceutical forms described above has given excellent results in the following pathological states: renal and hepatic colic, spasms of the viscera, the bladder and the urinary ducts; gastralgia cystitis, colitis and in general in pathological spastic and painful syndromes of the following organs and systems:

a. The gastro-intestinal system
b. bile ducts and gall-bladder tracts
c. urinary tracts and bladder d. female genital system.

Activity is exhibited both in acute forms, with painful spasms of high entity in which the parenteral forms are particularly active, as well as in chronic forms, in which on the contrary oral forms are selectively to be advised.

Interesting results for each of the compounds are also reported in vascular human diseases such as obliterating arteriopathies of sclerotic or diabetic origin, Bürgers' Disease, Rayraud's Disease, acrocyanosis, nocturnal cramps, paresthesia, claudicatio intermittens.

We claim:

1. A tyrosine compound of the formula:

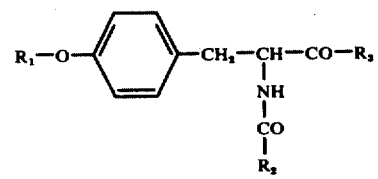

wherein: $R_1$ is linear or branched chain alkyl of 2–5 carbon atoms terminated by a tertiary amino group, wherein the tertiary amino group is dimethylamino, diethylamino, di-n-propylamino, di-isopropylamino, di-isobutylamino, methylethylamino, pyrrolidino, piperidino or N- substituted piperazino wherein the substituent is methyl, 2-Hydroxyethyl or benzyl; $R_2$ is phenyl, mono or di-substituted phenyl, wherein the substituents are -cl, -Br, $-NO_2$, $-OCH_3$, $-CH_3$ or $-CF_3$; $R_3$ is a monoalkylamino group of 1–6 carbon atoms, dialkylamino of 2 to 8 carbon atoms, pyrrolidino, piperidino or morpholino; or the pharmaceutically acceptable acid addition salts thereof.

2. A compound of claim 1, wherein the monoalkylamino group is selected from the class consiting of methylamine, ethylamine, n-propylamine, n-butylamine, n-hexylamine, isopropylamine and isobutylamine.

3. A compound of claim 1 wherein $R_3$ is dimethylamino, diethylamino, di-n-propylamino, di-n-butyl amino, di-isobutylamino, methylethylamino, pyrrolidino, piperidino or morpholino.

4. O-(2-diethylamino-ethyl)-N-benzoyl-DL-tyrosil-di-n-propylamide or the pharmaceutically acceptable acid addition salts thereof.

5. O-[3-(N''-methyl-piperazino)-N'-propyl]-N-(p-chlorobenzoyl)-DL-tyrosil-di-n-propylamide or the pharmaceutically acceptable acid addition salts thereof.

6. O-(2-diethylamino-ethyl)-N-(p-chloro-benzoyl)-DL-tyrosil-di-n-propylamide or the pharmaceutically acceptable acid addition salts thereof.

7. O-(3-diethylamino-propyl)-N-benzoyl-DL-tyrosil-di-n-propylamide or the pharmaceutically acceptable acid addition salts thereof.

8. O-(2-pyrrolidil-N'-ethyl)-N-toluoyl-DL-tyrosil-n-butylamide or the pharmaceutically acceptable acid addition salts thereof.

9. An antispatic pharmaceutical preparation consisting essentially of an effective amount of a compound of claim 1 and a pharmaceutically acceptable carrier.

10. A vasodilatory pharmaceutical preparation consisting essentially of an effective amount of a compound of claim 1 and a pharmaceutically acceptable carrier.

11. A compound of claim 1, wherein, $R_1$ is a linear alkyl group having 2-3 carbon atoms, terminated by a group selected from the class consisting of diethylamino, pyrrolidino and N'-methyl-piperazino; $R_2$ is selected from the class consisting of unsubstituted and monosubstituted phenyl groups, the substituent being in p-position and consisting of chlorine or methyl; $R_3$ is monoalkylamino of 3-4 carbon atoms, dialkylamino of 4-6 carbon atoms, pyrrolidino, piperidino or morpholino.

* * * * *